US00RE35803E

United States Patent [19]

Lange et al.

[11] E Patent Number: Re. 35,803

[45] Reissued Date of Patent: May 19, 1998

[54] BLOOD LANCET DEVICE FOR AND METHOD WITHDRAWING BLOOD FOR DIAGNOSTIC PURPOSES

[75] Inventors: Hans Lange, Lampertheim; Dirk Böcker, Heidelberg; Hermann Edelmann, Tutzing; Wolfgang Rüdinger, Birkenau; Herbert Argauer, Pirk, all of Germany

[73] Assignee: Boehringer Mannheim GmbH, Mannheim, Germany

[21] Appl. No.: 609,627

[22] Filed: Mar. 1, 1996

Related U.S. Patent Documents

Reissue of:

[64] Patent No.: 5,318,584
Issued: Jun. 7, 1994
Appl. No.: 987,612
Filed: Dec. 9, 1992

[30] Foreign Application Priority Data

Apr. 13, 1992 [DE] Germany ..... 42 12 315.1

[51] Int. Cl.[6] ..... A61B 17/32

[52] U.S. Cl. ..... 606/182; 606/181; 606/167

[58] Field of Search ..... 606/167, 181, 606/182, 184, 185, 188, 189; 128/760, 770, 898

[56] References Cited

U.S. PATENT DOCUMENTS

| | | | |
|---|---|---|---|
| 3,358,689 | 12/1967 | Higgins | 606/182 |
| 3,742,954 | 7/1973 | Strickland . | |
| 3,797,488 | 3/1974 | Hurschman et al. | 604/136 |
| 4,203,446 | 5/1980 | Hofert et al. | 606/182 |
| 4,442,836 | 4/1984 | Meinecke et al. | 606/182 |
| 4,469,110 | 9/1984 | Slama | 128/770 |
| 4,535,769 | 8/1985 | Burns | 606/182 |
| 4,643,189 | 2/1987 | Mintz | 606/182 |
| 4,850,973 | 7/1989 | Jordan et al. . | |
| 4,895,147 | 1/1990 | Boddicky et al. | 606/182 |
| 4,924,879 | 5/1990 | O'Brien | 606/182 |
| 5,324,303 | 6/1994 | Strong et al. . | |
| 5,423,847 | 6/1995 | Strong et al. . | |
| 5,454,828 | 10/1995 | Schraga . | |
| 5,480,387 | 1/1996 | Gabriel et al. . | |

OTHER PUBLICATIONS

Glucolet 2, Literature from "Miles Diagnostic Division", 1992.

*Primary Examiner*—Michael Peffley
*Attorney, Agent, or Firm*—Barnes & Thornburg

[57] ABSTRACT

Blood lancet device for withdrawing blood for diagnostic purposes, in which with the aid of a lancet drive (3) in a housing (1) a lancet holder (6) with a lancet (34) positioned in it and moveable along a predetermined, straight puncture path is moved until the tip (35) of the lancet emerges from the outlet (84), in order to produce a wound in a body part adjoining the outlet (84). The lancet holder (6) also serves to retract the lancet (34) into a position in which the tip (35) is again positioned within the housing (1).

In order to make possible a puncture involving especially little pain, the lancet drive (3) has a rotary/sliding transmission system (4) whose input side (16) is formed by a transmission member which is rotatable about an axis of rotation parallel to the predetermined puncture path. This input-side transmission member (5) of the rotary/sliding transmission system is coupled with the elastic drive element (9) of the lancet drive (3) and converts a torque transmitted to the transmission member (5) into a longitudinal displacement in the direction of the predetermined puncture path, which is transmitted to the lancet holder (6).

*A method for withdrawing blood for diagnostic purposes using the blood lancet device is also presented.*

58 Claims, 9 Drawing Sheets

BLOOD LANCET DEVICE FOR AND METHOD WITHDRAWING BLOOD FOR DIAGNOSTIC PURPOSES

Figure 1:
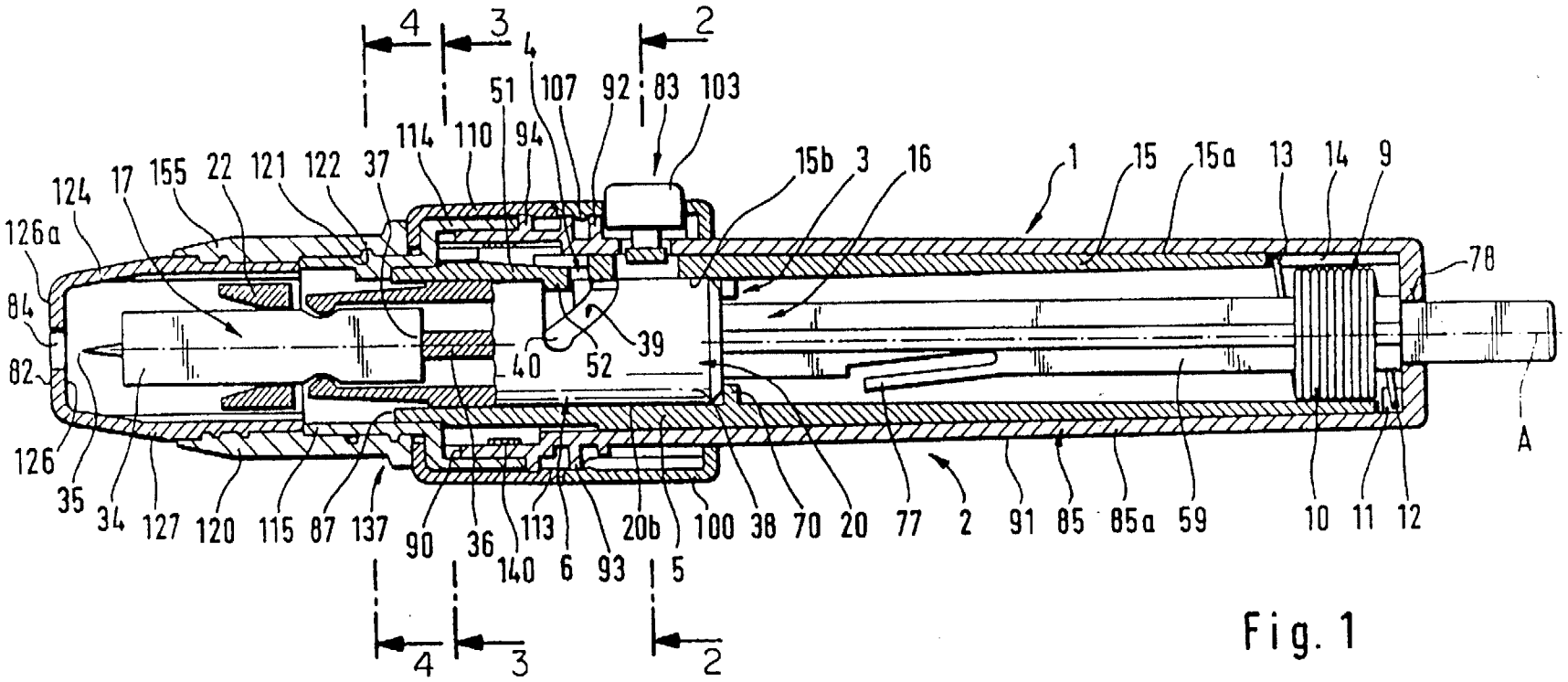

Matter enclosed in heavy brackets [ ] appears in the original patent but forms no part of this reissue specification; matter printed in italics indicates the additions made by reissue.

The invention relates to a blood lancet device for withdrawing blood for diagnostic purposes, said blood lancet device having a housing with an outlet for the tip of a lancet, a lancet holder for holding the lancet and movable within the housing along a predetermined, straight puncture path, and a lancet guide for guiding the lancet holder on the predetermined, straight puncture path. During the puncturing and retraction movement the lancet holder is moved by a lancet drive, which has an elastic drive element, commonly a metal spring. It is lockable in an initial position, in which the elastic drive element is in a tensioned state, by the use of a locking device. After the locking device is unlocked, the elastic drive element is released, and its movement is converted via the lancet drive into the puncturing movement, the lancet held in the lancet bolder being moved at high speed along the predetermined puncture path in the puncturing direction until its tip emerges from the outlet, in order to produce a wound in a body part pressed against the outlet (finger or ear lobe). Immediately thereafter the lancet is retracted by the lancet drive.

In order to obtain a small volume of blood from the finger or ear lobe for diagnostic purposes, in medical practice lancets are used, these being pricked into the appropriate body part by the doctor or laboratory personnel manually or with the use of a simple piece of apparatus. The lancet must, of course, be sharp and sterile. However, no other particularly stringent requirements are stipulated in medical practice because withdrawals of blood in individual patients are performed at long time intervals, and the puncture is performed by trained, specially educated personnel.

By contrast, the requirements relating to blood lancet devices intended for use by the patient himself are considerably more stringent. They are necessary above all to enable particularly high-risk patients groups to monitor specific analytical values in their blood on a regular basis within the scope of home-monitoring.

This applies in particular to diabetics, who must monitor their blood glucose level frequently and regularly in order to keep within specified reference limits as constantly as possible by adjusting their insulin injections to requirements, which depend on food intake, physical activity, and other factors. This is extremely important for the health of these patients and to avoid serious delayed damage, for example blindness and amputation of body parts.

For this reason small, simple to use and relatively low-cost analysis systems have been developed, usually comprising blood test strips and an accessory evaluation instrument. Although these have meant that the opportunity of analysis can now be offered to all patients without problems and at relatively low cost, self-monitoring of blood glucose values has not yet become as widespread among diabetics as one would like. A principal reason for this is the pain associated with the production of the puncture wounds necessary for the withdrawal of blood.

Numerous different blood lancet devices intended as suitable for producing the puncture wounds necessary for the withdrawal of blood easily and with relatively little pain have been developed. Examples are described in U.S. Pat. Nos. 4,442,836, 4,469,110, 4,535,769 and 4,924,897. Blood withdrawal instrument and lancet are mutually adapted, and are also described as a blood sampling system. Despite some progress, even with these known blood lancet devices intended in particular for use by the patient himself, the pain produced by the puncture is still excessive.

An object of the present invention is therefore to provide a blood lancet device which in a simple construction will perform the puncture in such a way as to lead to a reduced perception of pain.

In a blood lancet device of the type initially described this object is achieved according to a first principal aspect of the invention in that the lancet drive has a rotary/sliding transmission system which has a transmission member rotatable about an axis of rotation parallel to the predetermined puncture path and via which a torque introduced on the input side of the rotary/sliding transmission system is converted into a longitudinal displacement in the direction of the predetermined puncture path, the rotatable transmission member of the rotary/sliding transmission system is coupled with an elastic drive element, and the output-side longitudinal displacement of the rotary/sliding transmission system is transmitted to the lancet holder.

The term "transmission system" is employed here in the general sense, that is, as a kinematic device used for the coupling and conversion of movements, in the present case the movement during the release of the elastic drive element (which hereinafter without limiting the general applicability is also described as a drive spring) being converted into the movement of the lancet holder and of a lancet which is held in it preferably exchangeably.

The rotary movement of the input-side transmission member is preferably converted into a translational movement parallel with the axis of rotation of said transmission member with the aid of a cam drive mechanism, at least part of the puncturing movement and preferably also of the retraction movement being determined by a relative movement of a driver pin in a recess forming the driver cam, in which the pin travels along a driver cam formed by the recess. The recess which forms the driver cam may be provided either in the component forming the rotatable transmission member, or in an adjacent displaceable component. Correspondingly, the pin is rigidly connected either to an adjacent displaceable component or to the component forming the rotatable transmission member.

In the preferred design, the rotatable transmission member of the rotary/sliding transmission system has a cylindrical sleeve within which is located a piston-shaped part which, during longitudinal displacement in the direction of the puncture path, slides with a cylindrical outer wall within the sleeve, in which case the sleeve should be rotatable, but not displaceable in the axial direction, and the axially displaceable piston-shaped part located within it should be non-rotatable. In this case the piston-shaped part is preferably a component part of the lancet holder or firmly connected to it.

The blood lancet device according to the invention is characterised above all in that the vibrations during the puncturing and retraction movement are very slight because, apart from the lancet holder itself, no other components are accelerated and braked in the puncturing direction. Within the scope of the invention it has been found that this low level of vibration greatly contributes to a painless puncture.

Furthermore, the invention permits a simple construction of the drive with little play with few components and good guiding of the lancet holder. Vibrations during the puncturing and retraction movement are thereby largely avoided with low costs of manufacture. As was observed within the scope of the invention, this too is a major contribution towards reducing the perception of pain.

In addition, the invention allows a handy and compact construction, in which the housing preferably has an elongated shape ("pencil shape"), and its longitudinal axis runs parallel to the puncturing direction. This permits convenience of storage and simplifies operation.

According to a second principal aspect of the investigation, which should not only be regarded as a preferred embodiment but also has independent importance, the lancet drive and the holding of the lancet in the lancet holder are designed in such a way that the puncture depth at which during the puncturing movement the lancet tip emerges from the outlet varies by no more than at most 0.15 mm, preferably by at most 0.1 mm, and especially preferably by at most 0.05 mm with unchanged setting of the blood lancet device and successive puncturing movements.

The puncture depth should be easily and precisely adjustable by the user. In addition, the adjustment range preferably includes unusually low puncturing depths of between 0.5 mm and 2.0 mm, the range between 0.7 mm and 1.3 mm being of particular importance. Within the scope of the present invention it has been observed that, surprisingly, the blood volume required in medical practice for analysis, commonly between 1 and 50 μl and in the majority of cases between 10 and 30 μl, can be obtained with distinctly reduced pain in the overwhelming majority of people even at these low puncture depths, if an extremely high reproducibility of the depth of the puncture at a specific, unchanged setting of the apparatus is simultaneously ensured.

Admittedly a reproducible puncture depth is also aimed for with previously known blood lancet devices, such as that described in U.S. Pat. No. 4,442,836. Investigations in the context of the present invention have, however, shown that in all conventional blood lancet devices the variations in the puncture depth during successive puncture movements considerably exceed the previously mentioned limit values (at least about ±0.3 mm). The setting mechanism for setting the puncture depth is preferably designed so as to be adjustable stepwise, the interval between steps being at least about 0.2 mm and at most about 0.4 mm, preferably about 0.3 mm, at least within the above-mentioned preferred adjustment range (0.5 to 2.0 mm preferably 0.7 to 1.3 mm). The complete adjustment range can of course extend beyond the partial ranges mentioned and also include greater puncture depths in order to take account of the requirements of the relatively few individuals in whom an insufficient blood volume can be obtained with the deep puncture depths mentioned (for example owing to a particularly thick stratum corneum).

The reproducible puncture depth can be achieved by known mechanical means as long as relatively high-grade materials are used during manufacture and close tolerances are observed in production. However, the lancet drive described in connection with the first principal aspect of the invention is especially preferred.

A considerable improvement in the reproducibility of the puncture depth is achieved via a preferred embodiment in which the metal needle of the lancet has a positioning element and the lancet holder a stop for the positioning element, and the lancet is held in the lancet holder in such a way that the positioning element is pressed elastically against the stop.

Lancets always have a metal needle with one end ground to a point. The posterior part of the lancet needle at the opposite end from the tip is commonly enclosed in a lancet body made of a plastic material (U.S. Pat. No. 3,358,689). During manufacture the lancet needle is usually positioned in a plastic injection mould and the lancet body injected onto it. Lancets of this type are fixed in the lancet holder with the aid of the lancet body. The depth of the puncturing movement is usually limited in that, during the puncture, the anterior edge of the lancet body impinges on a stop rigidly connected with the lancet device housing in the zone of the blood lancet outlet. The puncture depth is also influenced by several tolerances. Above all, within the scope of the present invention it has been observed that the production tolerance of the position of the needle tip relative to the position of the plastic body is an important reproducibility-impairing factor.

In this proposed design the variation in the puncture depth from one lancet to another is influenced only by the tolerance of the distance between the positioning element and the tip of the metal needle. As illustrated below using examples, the positioning element can be formed by the posterior end of the needle, or by a projection positioned at a distance to one side of the needle. In this way, it is perfectly possible to maintain very close tolerances for the distance between the positioning element and the lancet tip by the usual metal working techniques.

Figure 2:
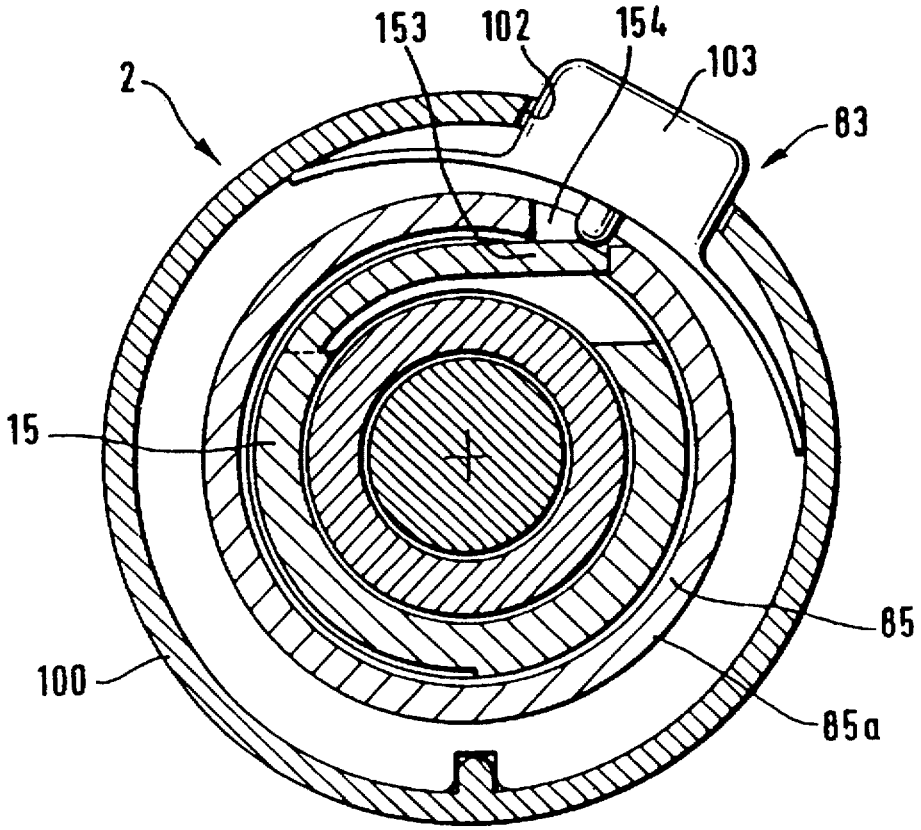
Figure 3:
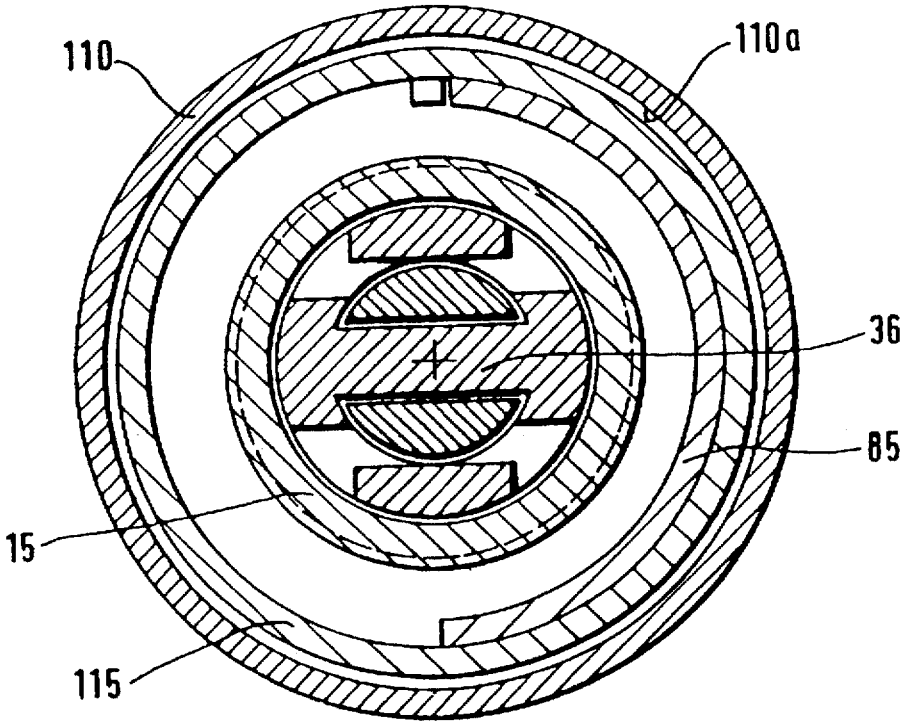
Figure 4:
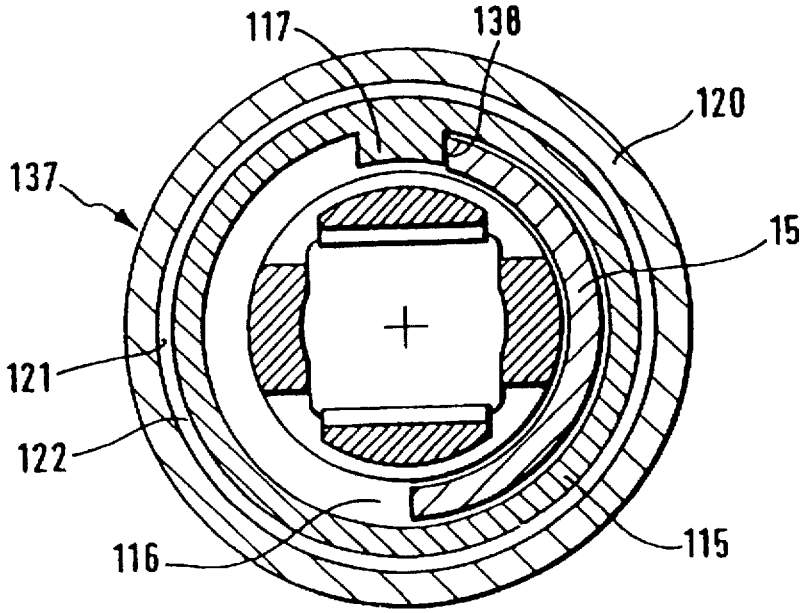
Figure 5:
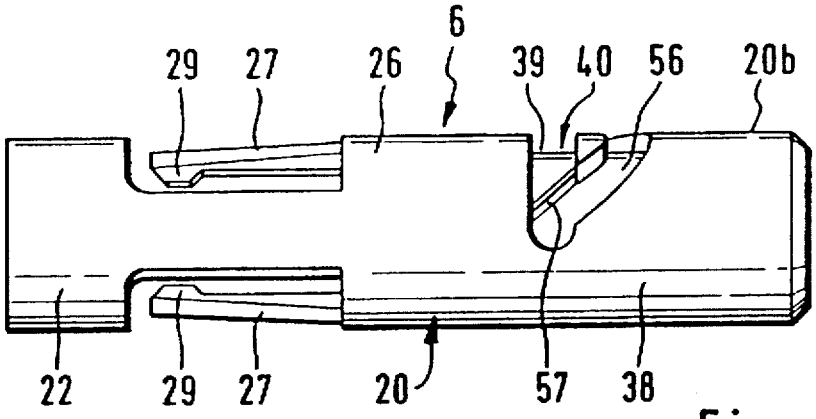
Figure 6:
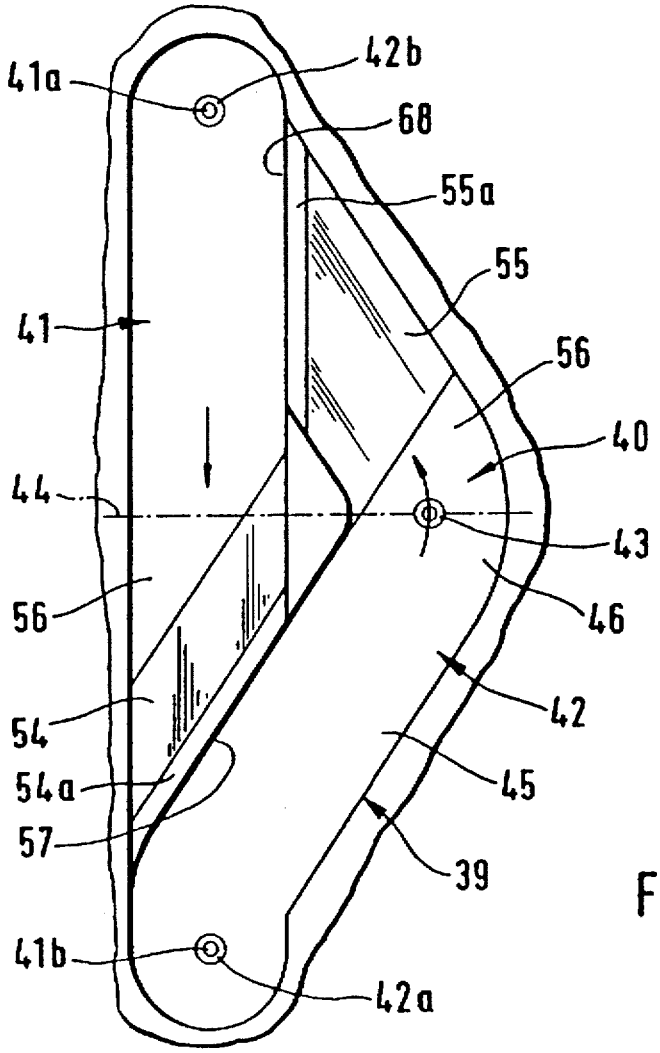
Figure 7:
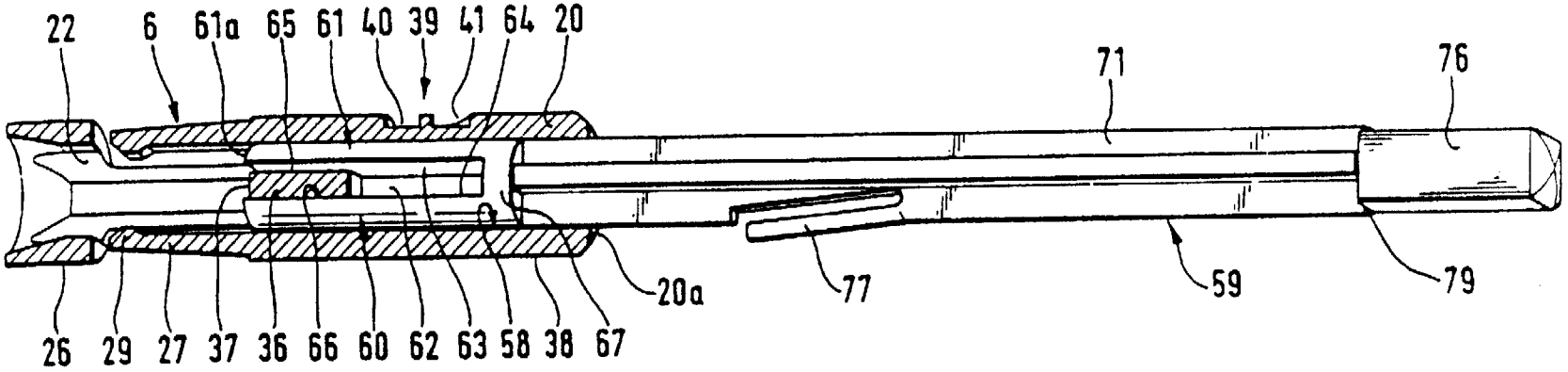
Figure 8:
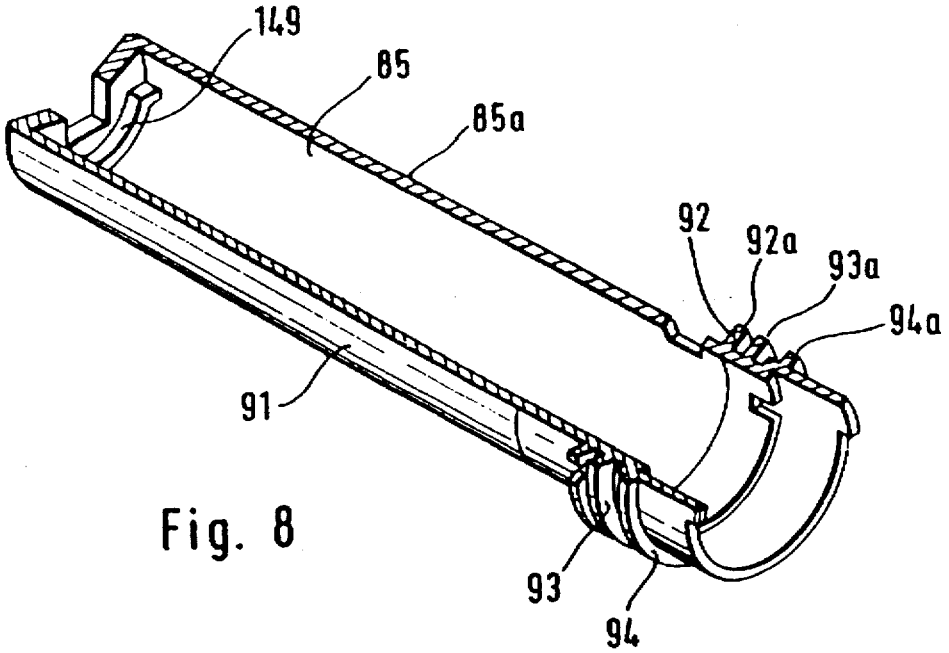
Figure 10:
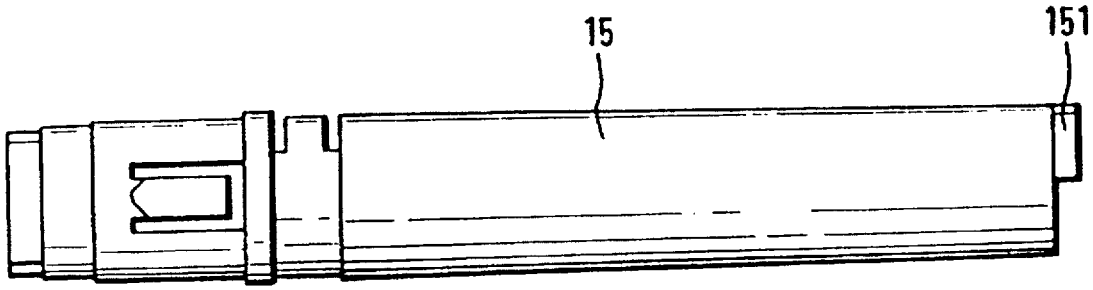
Figure 9:
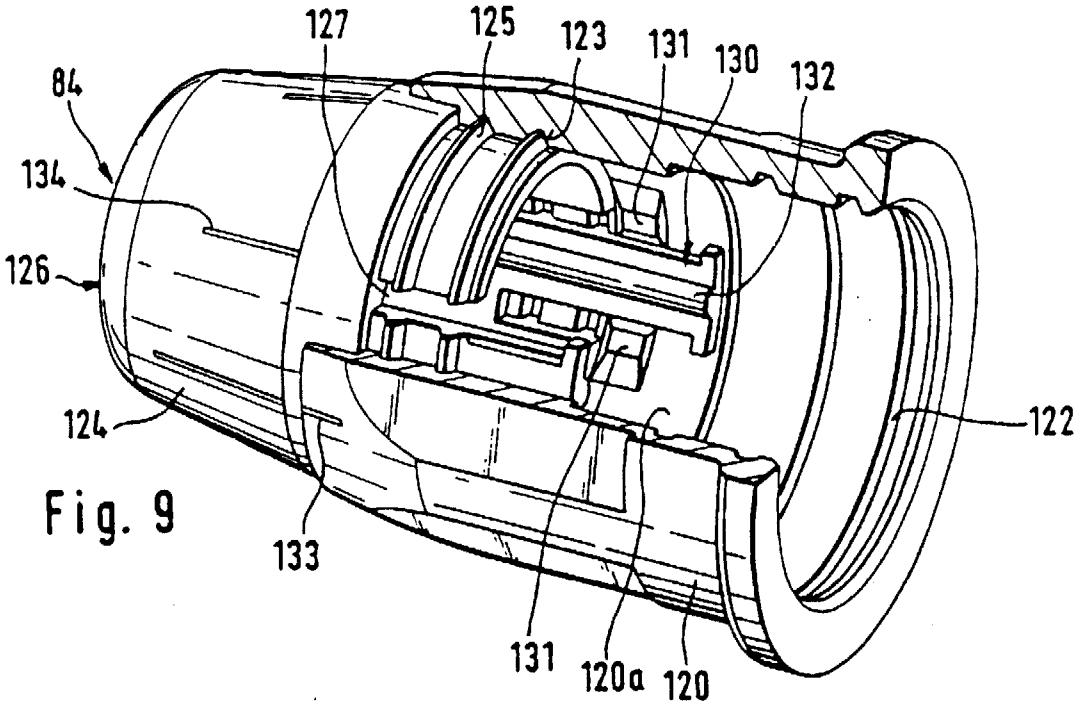
Figure 11:
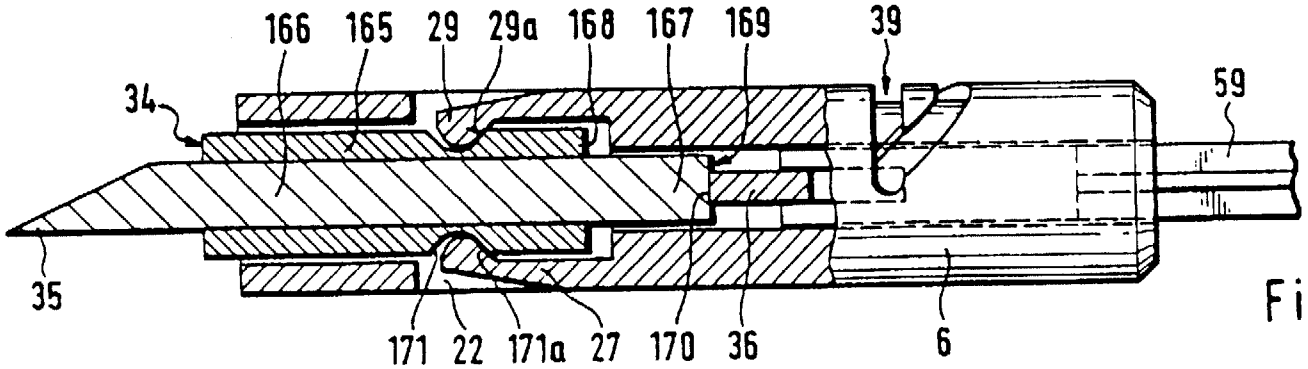
Figure 13:
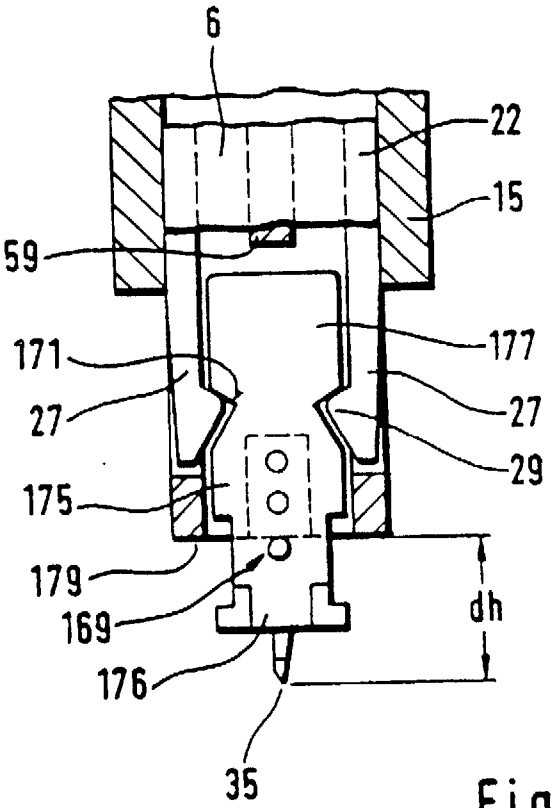
Figure 12:
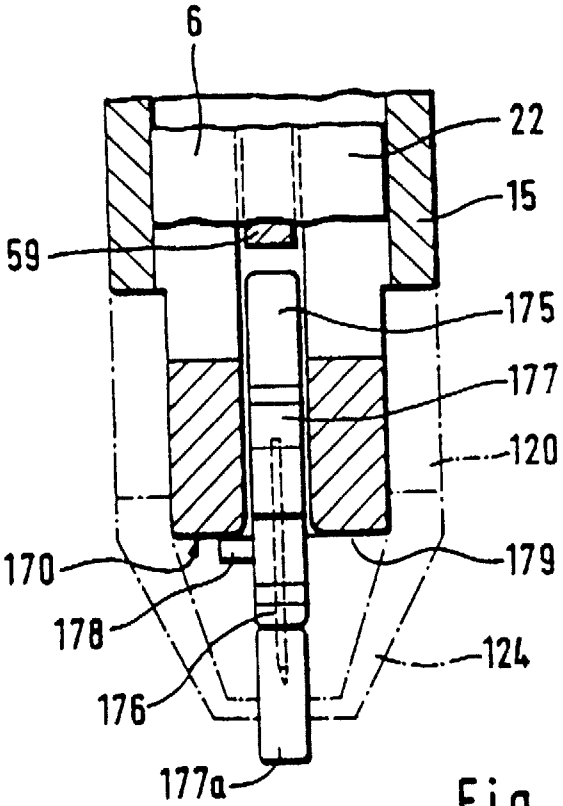
Figure 14:
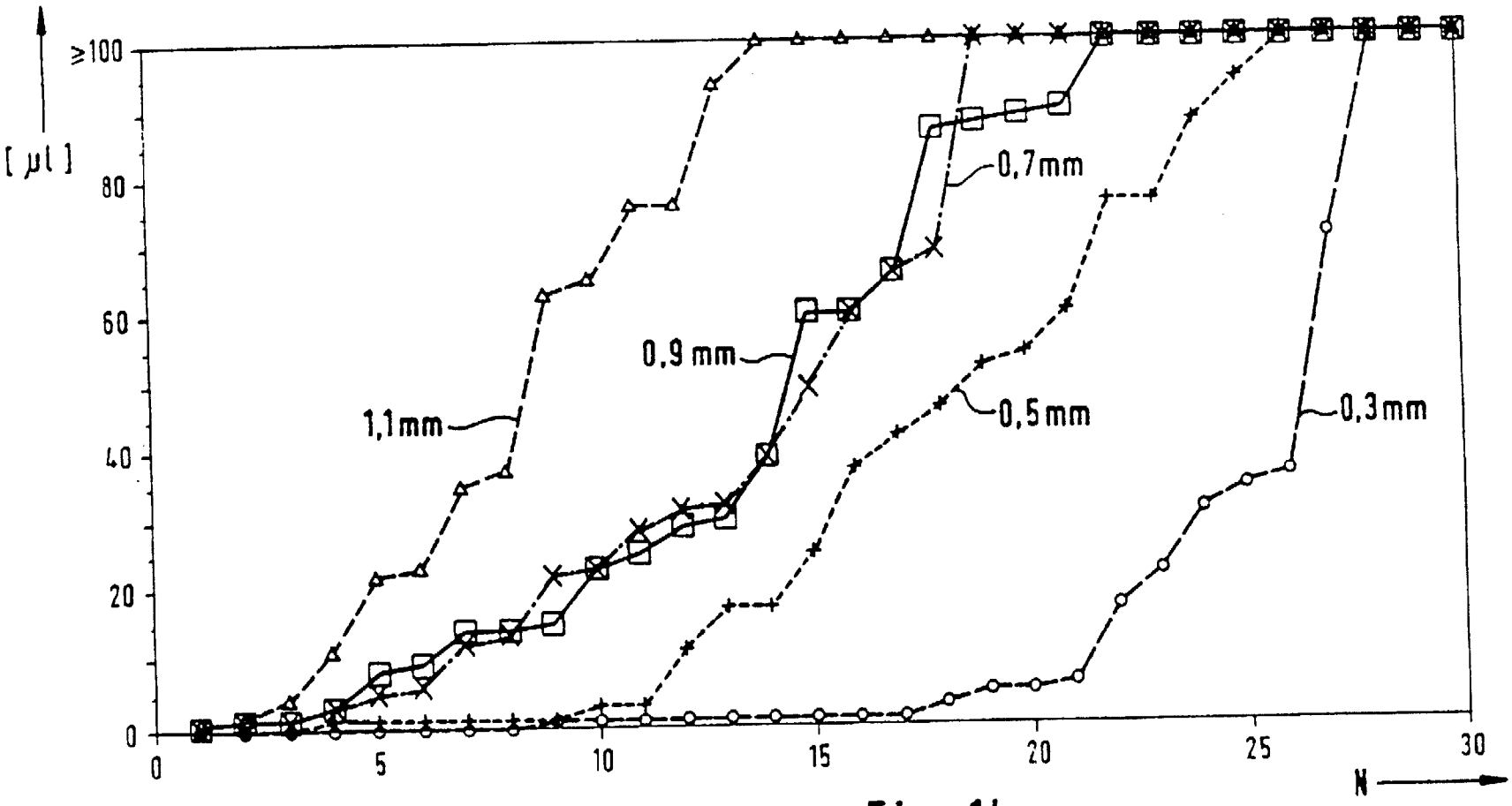

The invention is explained in greater detail below using an example of an embodiment schematically represented in the following figures:

FIG. 1 A longitudinal sectional view of a blood lancet device;

FIG. 2 A sectional view of a blood lancet device according to FIG. 1 along the line 1—1;

FIG. 3 A sectional view of a blood lancet device according to FIG. 1 along the line 2—2;

FIG. 4 A sectional view of a blood lancet device according to FIG. 1 along the line 3—3;

FIG. 5: A side view of the lancet holder of the blood lancet device according to FIG. 1;

FIG. 6: A projection of the contours of the driver cam recess of the lancet holder according to FIG. 5 in one plane;

FIG. 7: A partially cutaway diagram of the ram and lancet holder of a blood lancet device according to FIG. 1;

FIG. 8: A perspective sectional view of the housing cylinder of a blood lancet device according to FIG. 1;

FIG. 9: A partially cutaway diagram of a sealing sleeve and sealing cap of a blood lancet device according to FIG. 1;

FIG. 10: A side view of the cylindrical sleeve of a blood lancet device according to FIG. 1;

FIG. 11: A preferred embodiment of the lancet holding device and lancet, partly in side view and partly in sectional view;

FIGS. 12 and 13: two orthogonal sectional views of an alternative preferred embodiment of the lancet holding device and lancet;

FIG. 14: A graphical representation illustrating the function of the invention.

Within the housing 1 of the blood lancet device 2 shown in FIG. 1 a lancet drive 3 is located, said drive having a rotary/sliding transmission system 4 with a rotatable input-side transmission member 5 and a lancet holder 6 displaceable in the direction of the axis of rotation A of the transmission member 5. The torque introduced on the input side 16 of the rotary/sliding transmission system 4 is produced by an elastic drive element 9 of the lancet drive 3.

In the preferred embodiment described, the elastic drive element 9 is a spirally wound coiled spring 10. This is supported against a spring stop 11 on the housing 1 with one end 12, and with the other end 13 into an axial slit 14 on the input side (right-hand side in the figure) of the transmission member 5, which takes the form of a cylindrical sleeve 15. The spirally wound coiled spring 10 is located co-axially to the axis of rotation A of the rotary/sliding transmission system 4.

Positioned within sleeve 15 is lancet holder 6. A piston-shaped part 20, whose outer diameter is somewhat smaller than the internal diameter of sleeve 15 is a component part of lancet holder 6, and with its cylindrical outer wall 20b can slide along the internal wall of sleeve 15. The internal wall of sleeve 15 thus forms a lancet guide 15b during the puncturing and retraction movement. The sleeve 15 is fixed in housing 1 regarding axial displacement, and can rotate only about axis of rotation A.

Lancet holder 6 is overall designed roughly as a hollow cylinder with an approximately constant internal diameter (FIG. 5 and FIG. 7). In the lancet take-up part 22 lancet holder 6 is provided with two notches in its casing wall 26, into which two symmetrical and roughly axially parallel tongues 27 extend. These are each connected on one side to the piston-shaped part 20. The free end of both tongues 27 is formed into a lug 29, the distance between said lugs in the non-tensioned state of tongues 27 being smaller than the internal diameter of lancet holder 6. If a lancet 34 (shown in FIG. 1) is positioned in lancet holder 6, tongues 27 with the elastically inwardly pressed lugs 29 formed on them grip lancet 34 like a pair of tongs. The posterior end of lancet 34 adjoins the face 37 of a stay 36, which is diametrically located in lancet holder 6.

As can be seen in FIG. 1, FIG. 5, FIG. 7 and FIG. 11, the casing 38 of piston-shaped part 20 is provided with a groove-shaped recess 39 with a rectangular cross-section, said recess forming a driver cam 40 for rotary/sliding transmission system 4. The line of the contours of recess 39 in one plane is shown in FIG. 6. It will be recognised that recess 39 has two cam segments 41, 42 with constant groove width. The fist cam segment 41 is formed along a circumferential line of casing 38 of cylindrical part 20, in the preferred case described the angular distance between the start 41a and the end 41b of the first cam segment 41 being about 140°. In the zone of the end 41b of the first cam segment, recess 39 changes into the second cam segment 42 which, with identical groove width, connects the start 41a and the end 41b of the first cam segment 41. In so doing the second cam segment 42 follows an arcuate course. Like the first cam segment 41, it is located symmetrically in relation to axis 44. At the start 42a the second cam segment 42 has a straight piece 45 which steadily changes into a curved piece 46 which after an apex 43 travels symmetrically to axis 44 to the end 42b. Here too the end 42b of the second cam segment 42 corresponds to the start 41a of the first cam segment. The two cam segments 41, 42 form the annularly closed driver cam 40.

Positioned on the cylindrical sleeve 15 (FIG. 1) is a roughly axially parallel elastic tongue 51 attached on one side, at the free end of which there is a driver pin 52 which points into the interior of the sleeve 15, said driver pin engaging with the recess 39 of the piston-shaped part 20 and being able to travel along the driver cam 40 formed by recess 39 via a relative movement with the piston-shaped part. The groove width of recess 39 is co-ordinated with the diameter of the cylinder of driver pin 52 in such a way that, at least over the greater part of driver cam 40, driver pin 52 is positively interlocked with recess 39. In order to set the relative movement between driver pin 52 and recess 39, a ramp-like step 54, 55 is provided ahead of the end 41b, 42b of each of the two cam segments 41, 42 in recess 39 (FIG. 6), said ramp-like step 54, 55 rising evenly from the groove base 56, then finishing with a flank 57, 68 dropping perpendicularly to groove base 56. Thus, at the end of each cam segment 41, 42 driver pin 52 comes to lodge in such a way that it can move only in the direction of the end 41b, 42b of the other cam segment 41, 42.

Positioned in the cylindrical recess 58 of the piston-shaped part 20 is a cylindrical part 60 of a ram 59 (FIG. 7). The longitudinal axis of ram 59 corresponds to the longitudinal axis of lancet holder 6 and axis of rotation A of sleeve 15. Almost along its whole longitudinal axis, the cylindrical part 60 of ram 59 has a diametrical slit 62 via which the cylindrical part 60 of the ram forms a fork 61. The distance between the two plane-parallel surfaces 63, 64 of fork 61 is co-ordinated to the thickness of stay 36 in such a way that the cylindrical part 60 of ram 59 in the piston-shaped part 20 of lancet holder 6 is axially movable, the plane-parallel surfaces 63, 64 sliding over the two surfaces 65, 66 of stay 36. On the closed side 67 of the fork 61 ram 59 changes into a bar 71 with cruciform cross-section, said bar being located in such a way that it too can slide within the cylindrical recess 58 of piston-shaped part 20. Positioned at the end of ram 59 is an operating knob 76 with a roughly square cross-section.

On the bar 71 of ram 59 there is a tongue 77 which on impinging on a stay 70 of the cylindrical sleeve 15 limits the axial displacement of the ram 59 within the lancet holder 6.

Ram 59 is positioned in the blood lancet device 2 in such a way that the operating knob 76 projects through a corresponding opening 78 in housing 1, through which ram 59 is mounted non-rotatably with respect to housing 1 (FIG. 1). A ledge 79 formed at the transition of the bar 71 to the operating knob serves as the stop on housing 1 on axial displacement of ram 59. Bar 71 is inserted through the spirally wound coiled spring 10.

If driver pin 52 of cylindrical sleeve 15 is positioned at the start 41a of the first cam segment 41 of driver cam 40, coiled spring 10 is in a non-tensionned state (FIG. 1 and FIG. 6). By rotation of cylindrical sleeve 15 to the right, driver pin 52 within driver cam 40 of the piston-shaped part 20 is moved to the end 41b of the first cam segment 41, and coiled spring 10 coupled to sleeve 15 is induced into a tensioned state. The fact that ram 59 is non-rotatably mounted in housing 1 and stay 36 is positioned within fork 61 prevents lancet holder 6 from also rotating when the sleeve 15 rotates. During this rotation of sleeve 15 to the right no longitudinal displacement is executed by lancet holder 6, since the first cam segment 41 travels along a circumferential line of piston-shaped part 20. At the end of the slope of step 54 there is a non-sloping surface segment 54a which still is a little below the top edge of the side walls of cam 40. The bending stress of tongue 51 causes driver pin 52 to be pressed against groove base 56 at the end of the first cam segment 41b. Via vertical flank 57 of step 54, sleeve 15 with driver pin 52 is prevented from being able to move back along the first cam segment 41 due to the now tensioned state of coiled spring 10.

A locking device 83 locks the cylindrical sleeve 15 in this position of the driver pin 52 (FIG. 1 and FIG. 2). If the locking device 83 is released, the spring tension of coiled spring 10 causes a torque to be transmitted to the input side 16 of the rotary/sliding transmission system 4, sleeve 15 being rotated back in the opposite direction to the former direction of rotation and driver pin 52 travelling along the second cam segment 42 (FIG. 1 and FIG. 2). In the process, on the output side 17 of the rotary/sliding transmission system 4 piston-shaped part 20, which is fixed to prevent rotary movements, is displaced longitudinally within housing 1 in the direction of outlet 84 of said housing 1 until driver pin 52 has reached apex 43 of the second cam segment 42 and the tip 35 of the lancet 34 emerges through the outlet 84. When driver pin 52 is positioned at the apex 43 of the second cam segment 42, the tip 35 of the lancet 34 has reached its maximum longitudinal displacement in the direction of the puncture path.

Because the blood lancet device is pressed against the skin with a pressure surface 82 surrounding outlet 84, the puncture depth corresponds to the distance between tip 35 and pressure surface 82 (in the direction of the puncture path).

The retraction movement of the lancet 34 is complete when the driver pin has reached the end 42b of the second cam segment 42, which is identical with the start 41a of the first cam segment 41. Before it reaches this point it slides over the slope of a second ramp-like step 55, which again has a non-sloping surface segment 55a and a vertical flank 68 at its end. The slope here is longer and less steep in order to slow down the movement as little as possible. Because of this the driver pin 52 can only continue to move only along the first cam segment 41.

The puncturing and retraction movement of lancet 34 is achieved by converting the rotary movement about the axis of rotation A of the spirally wound coiled spring 10 and of transmission member 5 into a longitudinal displacement of lancet holder 6 in the direction of the predetermined puncture path and thereafter in the opposite direction.

In an alternative embodiment of the invention it can also be provided that the interlocking of recess 39 and driver pin 52 is present only in partial sections, in particular the section between the start 41a and the apex 43 of the second cam segment 42.

In the embodiment shown in FIG. 1, housing 1 of blood lancet device 2 comprises a number of elements. The cylindrical sleeve 15 is positioned in a housing cylinder 85 open on one side. Here, cylindrical sleeve 15 projects with its face 87 out of the open end 90 of the housing cylinder 85. On casing surface 91 of housing cylinder 85 in the area of the open end 90 there are three encircling stays 92, 93, 94 (FIG. 8), the first 92 and second 93 stay with their outer edges 92a, 93a being a greater distance away from casing surface 91 than the outer edge 94a of the third stay 94. On the outer edges 92a, 93a of these two stays 92, 93, a cover ring 100 is supported, which has an opening 102 for taking a key 103 for the release of locking device 83 (FIG. 2). On the first face, which points towards lancet tip 35, cover ring 100 is open whereas the second face is provided with a circular recess, the diameter of which roughly corresponds to the diameter of casing surface 91 of housing cylinder 85. For fixing housing cylinder 85, cover ring 100 has a torsion protection device and a bead 107 which follows a course along the casing internal surface in the direction of the circumference, said bead 107 being positioned between the first stay 92 and the second stay 93 of the housing cylinder 85 (FIG. 1).

Attached flush to the open end of cover ring 100 is an intermediate ring 110, which is supported on the second stay 93 of housing cylinder 85 and, with a bead 113 following a course on the inside in the direction of the circumference, on the third stay 94 of housing cylinder 85 (FIG. 1). The intermediate ring 110 surrounds an extended collar 114 of a tension sleeve 115. The tension sleeve 115 has been axially pushed roughly in the position of the lancet take-up part 22 onto the cylindrical sleeve 15 and is fixed with this regarding displacement in the direction of the longitudinal axis. In addition, a notch 116 is provided in the casing of the cylindrical sleeve 15 along a roughly hemi-circumferential line, with which notch 116 a gripping device 117 of the tension sleeve 115 engages (FIG. 4).

For screwing on a sealing ring 120, on the end of the tension sleeve 115 facing outlet 84 there is an outer thread 121, while sealing ring 120 is provided with a corresponding internal thread 122 (FIG. 1 and FIG. 9). By means of a second internal thread 123 a sealing cap 124 with an external thread 125 is screwed into the end of sealing ring 120 facing outlet 84. Sealing cap 124 is closed at the fist face 126 with the exception of puncture opening 84, the outer surface 126a of face 126 being placed on an area of skin during the use of the blood lancet device 2. The puncture depth is set using thread 123, 125, with which sealing cap 124 and sealing ring 120 are connected.

Lancet drive 3 and adjustability via thread 123, 125 are so co-ordinated with the dimensions of the lancet 34 to be used that the puncture depth is adjustable within a desired adjustment range, which in a preferred practical embodiment ranges from 0.7 mm to 2.2 mm, successive puncture movements with unchanged setting of the blood lancet device 2 varying in respect of the puncture depth by at most 0.15 mm, preferably by at most 0.1 mm, and especially preferably by at most 0.05 mm.

In order that the user of the blood lancet device 2 can set what is, for him, the optimal puncture depth step-wise and not have to make a re-adjustment with each use, an engaging device 130 is envisaged, as FIG. 9 shows. To this end, on its casing internal surface 120a sealing ring 120 is provided with radially encircling, evenly distributed nubs 131. Between each pair of these nubs 131 there lodges an engaging tongue 132, which is fastened to sealing cap 124 on one side and parallel to the longitudinal axis on casing 127 of sealing cap 124 so that it lodges almost free of play in the free zone between two nubs 131. By twisting of sealing cap 124 and sealing ring 120 in opposite directions, the elastically formed engaging tongue 132 slides past a nub 131 and comes to lodge in the next free zone between two nubs 131. To monitor the puncture depth, sealing ring 120 bears a mark 133, with the aid of which the puncture depth set can be read off against a scale 134 on sealing cap 124.

By rotation of the sealing ring 120 of the tensioning device 137 to the right with respect to the housing cylinder 85, the tensioning sleeve 115 with the cylindrical sleeve 15, which are engaged with the catch 117 and the first face 138 of the notch 116, is also turned (FIG. 1 and FIG. 4). The blood lancet device 2 is thereby tensioned. At the start of the rotation to the right, driver pin 52 is at the start of the first cam segment 41 and travels along this to the end 41b, step 55 positively determining the direction of movement. During this rotation to the right, lancet holder 6 remains in its position in housing 1 without executing a movement. This has the advantage that during the rotation to the right the lancet tip 35 does not emerge through opening 84, and an undesirable risk of injury due to the tensioning procedure is thereby excluded.

Simultaneously with the rotation to the right the spirally wound coiled spring 10 and an elastic retraction element, which in the described preferred embodiment is similarly in the form of a spirally wound coiled spring 140, are induced into a tensioned state. In the process, return spring 140 is supported on the one hand on the housing cylinder 85 and on the other on the tensioning sleeve 115 (FIG. 1). The rotation to the right is ended by the meeting of a stop stay 149 on the housing cylinder 85 and a stop lug 151 of the cylindrical sleeve 15 (FIG. 8 and FIG. 10). In the process driver pin 52 at end 41b of the first cam segment 41 comes to lodge behind the vertical flank 57 of step 54, and an elastic locking tongue 153 (FIG. 2) of the locking device 83 snaps into a corresponding locking recess 154 positioned on the casing 85a of the housing cylinder 85 and locks the blood lancet device 2 in the tensioned state.

The tensioning device 137 therefore has an operating element 155 (in the described preferred case the sealing ring 120) accessible from outside the housing 1, said operating element being coupled with the input side 16 of the rotary/sliding transmission system 4 in such a way that, by rotation of operating element 155 with respect to the housing 1, the elastic drive element 9 of the lancet drive 3 is induced into the tensioned state (FIG. 1).

On the release of the sealing ring 120, the spring tension of the return spring 140 comes into play and turns the mutually coupled elements consisting of the tensioning sleeve 115, sealing ring 120 and sealing cap 124 back into their starting position, the rotary/sliding transmission system 4 not being moved. Because the drive sleeve 15 is engaged only on rotation to the right of sealing ring 120, a free-wheeling function is achieved. Because operating element 155, after the tensioning of the drive element 9, is returned to the starting position, it remains at rest during the puncture movement.

After the release of the locking device 83 by pressing the button 103, the puncturing procedure is initiated. In the process the elastic locking pin 153 fastened to the drive sleeve 15 is moved from the locking recess 154 of the housing cylinder 85 into the interior space of the housing cylinder 85, as a result of which the drive sleeve 15 is released for rotary movements with respect to housing 1 (FIG. 2). The mounting of button 103 is designed in such a way that when the blood lancet device 2 is non-tensioned the button is held in a depressed position. Only in the tensioned state of the coiled spring 10 is the button 103 pressed outwards. The operating status of the blood lancet device 2 can thus be ascertained from the position of the button 103. The button 103 is enclosed by the covering ring 100, by which it is also held in place with respect to the housing 1.

The spring tension of the coiled spring 10 now introduces a rotation of the drive sleeve 15 to the left. During this rotation to the left, driver pin 52 travels along the second cam segment 42 of the driver cam 40, as described.

Because the blood lancet device 2 according to the invention has a small accelerated mass in the direction of the longitudinal movement of lancet 34, the puncture is very largely vibration-free. This is an important requirement for a puncture with little pain, as was demonstrated in investigations in the context of the invention. The described guiding of the lancet holder 6 within the rotary/sliding transmission system further contributes to the vibration-free and therefore also pain-free puncture.

To replace the lancet 34, sealing ring 120 with the sealing cap 124 is screwed off by rotation to the left. By pressing on the operating knob 76, ram 59 is moved in the direction of the outlet of the housing along the axis of rotation A (FIG. 1 and FIG. 7). In the process the face 61a of the fork 61 presses on lancet 34, which is thereby ejected. The axial movement of the ram 59 is limited by the tongue 77 of the ram, said tongue impinging upon the stay 70 of the cylindrical sleeve 15. The new lancet 34 is inserted into the lancet take-up part 22 of the lancet holder 6 and pushed in as far as the first face 37 of the stay 36. In the process the ram 59 is pushed back and the lancet 34 is gripped firmly by the two lugs.

In order to obtain good reproducibility of the puncture depth with unchanged setting of the blood lancet device 2, an exactly reproducible positioning of the lancet 34 in lancet holder 6 is necessary. The preferred embodiments for holding the lancet shown in FIGS. 11 to 13 serve this purpose.

The lancet 34 shown in FIG. 11 comprises as usual a plastic body 165 and a metal needle 166. It is however of a novel design in that the posterior end 167 of the metal needle 166 projects beyond the posterior end 168 of the plastic body 165. The rearward face of the posterior end 167 serves as the positioning element 169. Said positioning element adjoins a stop 170 of the lancet holder 7, which in the case shown is formed by stay 36.

The holding of the lancet 34 in the lancet holder 6 is designed in such a way that the lancet 34 is pressed back with positioning element 169 against stop 170 (in opposition to the puncturing direction). In the embodiment shown, this is achieved in that the V-shaped recesses 171, with which the lugs 29 of the elastic tongues 27 engage, are designed and disposed in such a way that the posterior sloping surface 29a adjoins a corresponding sloping surface 171a of the recesses 171 and a force component in opposition to the puncturing direction results from the pressure of the tongues 27 in the direction of axis A.

The body 165 of the lancet 134 is preferably not round but, for example, square. Via a corresponding shape of the interior space of the lancet take-up part 22 protection against torsion is ensured.

The embodiment shown in FIGS. 12 and 13 is distinctive above all in that the needle 176 is not round in cross-section, but consists of a thin flat material. The shape of the needle can be appreciated in FIG. 12 in side view of the narrow edge, and in FIG. 13 in side view of the surface.

FIG. 12 represents a tip protection device 177a removable by rotation, said tip protection device being injected—as is also common practice with other lancets—together with the plastic body 177 on to needle 176 and removed before the lancet is used.

The needle 176 is held in a plastic body 177, which in this case also has V-shaped recesses 171 which interlock with the lugs 29 of the elastic tongues 27 of the holder 6 in the same way as in FIG. 11 to produce a resultant force component which acts on the lancet in opposition to the puncturing direction.

In this case a peg-shaped projection 178 positioned at a distance to one side of the needle 176 serves as the positioning element 169, said projection 178 adjoining a lower face 179 of the take-up part 22 of the lancet holder 6 forming the stop 170.

A lancet of this type is easily manufactured in a punching process. Said lancet is characterised by particularly close tolerances of the distance between the lancet tip 35 and the positioning element 169 and thus by a particularly good reproducibility of the puncture depth. Furthermore, the flat shape permits a relatively broad construction of the lancet tip in the plane of needle 176. In this way a relatively large blood sample volume is achieved with little pain using a small puncture depth.

As mentioned above, in the context of the present invention it was observed that, surprisingly, an adequate volume of blood by comparison with the greatly reduced puncture depths commonly used in the past can be obtained if care is simultaneously taken to ensure that the puncture depth is very accurately reproducible.

In FIG. 14 results obtained in 30 test subjects with the blood lancet device according to the invention are presented in graph form. The number N of test subjects is plotted along the x-axis, and the blood volume obtained in μl along the y-axis. The five curves show the results using puncture depths of 0.3 mm, 0.5 mm, 0.7 mm, 0.9 mm, and 1.1 mm. It is seen that using a puncture depth of 0.3 mm, inadequate blood volumes were obtained in the great majority of cases. In the case of twenty-one patients the blood volumes were below 10 μl.

On increasing the puncture depth to 0.5 mm, and even more on further increasing it to 0.7 mm or 0.9 mm, the number of patients in whom an adequate blood volume was produced increased very markedly. For example, FIG. 14 shows that using puncture depths of 0.7 mm and 0.9 mm, blood volumes of 20 μl and above were already obtained in ⅔ of the test subjects. With modern analytical equipment this volume is frequently sufficient for an exact analysis.

Using a puncture depth of 1.1 mm the blood volume obtained once again distinctly increases. In this case it is below the 20 μl limit value only in 4 patients, i.e. fewer than 15% of the total number of participants.

Bearing in mind that previously known blood lancet devices commonly operate with puncture depths in excess of 2 mm in order to obtain an adequate quantity of blood, the present results clearly show that within the scope of the invention a marked reduction in pain is achievable in the large majority of patients via a reduction in the puncture depth, and that nevertheless an adequate blood volume can be obtained.

What is claimed is:

1. Blood lancet device for withdrawing blood for diagnostic purposes, comprising a lancet (34) comprising a metal needle (166,176) with a tip (35), a housing (1) with an outlet (84) for the tip (35) of the lancet (34), a lancet holder (6) located within the housing and connectable to the lancet (34) for holding the lancet (34), a lancet guide means (15b) located within the housing for guiding the lancet holder (6) for movement on a predetermined puncture path, and a lancet drive means (3) located within the housing for moving the lancet (34) in a puncturing and retraction direction comprising an elastic drive element (9), a locking device (83) for locking said lancet drive in a fist position in which the elastic drive element (9) is in a tensioned state and for releasing the tension of the elastic drive element (9) to accomplish a puncturing movement during which the lancet holder (6) is moved at high speed along the predetermined puncture path in a puncturing direction until the tip (35) emerges from the outlet (84) to produce a wound in a body part adjoining the outlet (84) and following which the lancet holder (6) is retracted to a position in which the tip of the lancet (34) is positioned within the housing.

the lancet drive (3) further comprising a rotary/sliding transmission system (4) with an input-side transmission member (5) rotatable about an axis of rotation (A) parallel to the predetermined puncture path and coupled to the elastic drive element (9) to be rotated thereby, and with an output-side transmission member connected to the rotatable input-side transmission member (5) for longitudinal displacing the lancet holder (6) in response to rotation of said input-side transmission member (5).

2. Blood lancet device according to claim 1, in which the rotary/sliding transmission system (4) comprising a cam drive mechanism with a recess (39) forming a driver cam (40), a driver pin (52) enagaging said recess such that at least a part of the puncturing and retraction movement is determined by a relative movement between the driver pin (52) and the recess (39), the drive pin (52) travelling along the recess (39).

3. Blood lancet device according to claim 1, in which the input-side transmission member (5) is in the form of a cylindrical sleeve (15) within which is located a piston-shaped part (20) which, during the longitudinal displacement in the direction of the puncture path, slides with a cylindrical outer wall (20b) within the sleeve (15).

4. Blood lancet device according to claim 3, in which the piston-shaped part (20) is connected to the lancet holder (6).

5. Blood lancet device according to claim 1, comprising a tensioning device (137) with an operating element (155) accessible from outside of the housing, said operating element being coupled to the input-side transmission member (5) of the rotary/sliding transmission system in such a way that the elastic drive element (9) can be brought into the tensioned state by rotation of the operating element (155) with respect to the housing (1).

6. Blood lancet device according to claim 5, in which the coupling of the operating element (155) of the tensioning device (137) with the rotary/sliding transmission system (4) has a free-wheeling mode and an elastic return element (140) in order to return the operating element (155) to the starting position after the tensioning of the drive element (9).

7. Blood lancet device according to claim 1, in which the locking device (83) comprising a locking pin (153) firmly connected with the input-side transmission member (5) and in the tensioned state of the lancet drive (3) engages with a stationary locking recess.

8. Blood lancet device according to claim 1, in which the elastic drive element (9) is a spatially wound coiled spring (10) located coaxially to the axis of rotation (A) of the rotary/sliding transmission system (4).

9. Blood lancet device for withdrawing blood for diagnostic purposes, comprising a lancet (34) comprising a metal needle (166, 176) with a tip (35), a plastic body (165) connected to said metal needle (166, 176), and a lancet positioning means (169, 178), a housing (1) with an outlet (84) for the tip (35) of the lancet (34), a lancet holder (6) located within the housing and contacting the lancet (34) for holding the lancet (34) and movable within the housing (1) along a predetermined puncture path, and a lancet drive means (3) located within the housing for moving the lancet in a puncturing direction comprising an elastic drive element (9), a transmission system driven by said elastic drive element to contact and move the lancet positioning means (169, 178) through a precisely defined maximum longitudinal displacement, and wherein the lancet holder accurately positions the lancet positioning means (169, 178) relative to the lancet drive (3) means such that the puncture depth at which during the puncturing movement tip (35) of the lancet (34, 175) emerges from the outlet (84) varies by no more than at most ±0.15 mm with unchanged setting of the blood lancet device and successive puncturing movements.

10. Blood lancet device according to claim 9 comprising means for adjusting the puncture depth of the lancet (34) within an adjustment range which includes adjustment values of less than 2 mm.

11. Blood lancet device according to claim 10, characterized in that the adjustment range includes adjustment values of less than 1.3 mm.

12. Blood lancet device according to claim 9, comprising means for adjusting the puncture depth of the lancet (34) in steps, the interval between steps being at least 0.2 mm and at most 0.4 mm.

13. Blood lancet device according to claim 9 in which said positioning means (169, 178) is accurately located with respect to the needle (166, 176) of the lancet (34) and a stop (170) on the lancet drive means (3), and wherein the lancet (34, 175) is held in the lancet holder (6) in such a way that the positioning means (169) is elastically pressed against the stop (170).

14. Blood lancet device according to claim 9 in which the puncture depth varies at most by ±0.1 mm.

15. Blood lancet device according to claim 14 in which said driver output member (40) is configured to have a cam segment 42 with an apex 43 which precisely defines the maximum longitudinal displacement of the needle (166, 176).

16. Blood lancet device according to claim 9 in which the puncture depth varies at most by ±0.05 mm.

17. Blood lancet device for withdrawing blood for diagnostic purposes comprising a lancet (34) comprising a metal needle (166, 176) with a tip (35) and a plastic body (165), a lancet holder (6) for holding the lancet (34), a lancet drive means (3) for driving the lancet needle (166, 176) along a predetermined straight path, the driving means comprising a driver input member rotatable about an axis parallel to the straight path, a driver output member connected to the lancet and the driver input member for converting the rotation of the driver input into longitudinal movement of the lancet along said straight path, and means for accurately positioning the metal needle (166, 176) of the lancet (34) relative to the driving means, thereby accurately to control the puncture depth of the tip (35), the positioning means comprising a positioning means surface (169) on the needle (166, 176), a stop (170) on the lancet holder (6) for abutting the positioning means surface (169), and elastic means for pressing the positioning means surface (169) against the stop (170).

*18. A method for withdrawing blood for diagnostic purposes by puncturing a patient using the blood lancet device of claim 1, said method comprising:*

*inserting the lancet into the lancet holder with a lancet positioning means surface on the lancet engaging a stop of the lancet holder which is connected to the output-side transmission member on the lancet drive means and wherein there is an elastic means for pressing the lancet positioning means surface against the stop;*

*holding the blood lancet device against the skin of a patient; and*

*actuating the lancet drive means to drive the lancet along the predetermined puncture path through a precisely defined longitudinal movement, wherein the needle tip will emerge from the blood lancet device and be driven into the skin of the patient.*

*19. A method according to claim 18, wherein the puncture depth can be varied without changing the precisely defined longitudinal movement by changing the relative position of the fully inserted needle tip with respect to the patient's skin.*

*20. A method according to claim 18, wherein the puncture depth of the needle tip into the patient varies by no more than at most 0.15 mm with unchanged setting of the puncture depth.*

*21. A method according to claim 20, wherein the puncture depth of the needle tip into the patient varies by no more than at most 0.1 mm with unchanged setting of the puncture depth.*

*22. A method according to claim 21, wherein the puncture depth of the needle tip into the patient varies by no more than at most 0.05 mm with unchanged setting of the puncture depth.*

*23. A method according to claim 18, wherein the puncture depth can be adjusted in an adjustment range which includes values of the puncture depth below 2 mm.*

*24. A method according to claim 23, wherein the puncture depth can be adjusted in an adjustment range which includes values of the puncture depth below 1.3 mm.*

*25. A method for withdrawing blood for diagnostic purposes by puncturing a patient using the blood lancet device of claim 17, said method comprising:*

*inserting the lancet into the lancet holder with the lancet positioning means surface engaging the stop on the lancet and wherein the elastic means presses the lancet positioning means surface against the stop;*

*holding the blood lancet device against the skin of a patient; and*

*actuating the lancet drive means to drive the lancet along the predetermined puncture path through a precisely defined longitudinal movement, wherein the needle tip will emerge from the blood lancet device and be driven into the skin of the patient.*

*26. A method according to claim 25, wherein the puncture depth can be varied without changing the precisely defined longitudinal movement by changing the relative position of the fully inserted needle tip with respect to the patient's skin.*

*27. A method according to claim 25, wherein the puncture depth of the needle tip into the patient varies by no more than at most 0.15 mm with unchanged setting of the puncture depth.*

*28. A method according to claim 27, wherein the puncture depth of the needle tip into the patient varies by no more than at most 0.1 mm with unchanged setting of the puncture depth.*

*29. A method according to claim 28, wherein the puncture depth of the needle tip into the patient varies by no more than at most 0.05 mm with unchanged setting of the puncture depth.*

*30. A method according to claim 25, wherein the puncture depth can be adjusted in an adjustment range which includes values of the puncture depth below 2 mm.*

*31. A method according to claim 30, wherein the puncture depth can be adjusted in an adjustment range which includes values of the puncture depth below 1.3 mm.*

*32. A method for withdrawing blood for diagnostic purposes by puncturing the skin of a patient utilizing a blood sampling system comprising a blood withdrawal instrument and disposable lancets wherein the blood withdrawal instrument comprises a housing with a needle outlet, a pressure surface surrounding the needle outlet, a drive means and a lancet holder for exchangeably holding the disposable lancets and wherein the disposable lancets comprise a metal needle embedded in a plastic body with the needle having a needle tip extending outwardly from a first end of the plastic body and a flat end accessible adjacent an opposite end of the plastic body, said method comprising:*

*inserting the disposable lancet, flat needle end forward, into the blood withdrawal instrument to a position in*

*which the flat end of the needle contacts a stop on the lancet holder and in which the lancet is accurately positioned relative to the lancet holder by being pressed against the stop by elastic means;*

*placing the pressure surface of the blood withdrawal instrument against the skin of the patient; and*

*actuating the lancet drive means to have the lancet drive means move the lancet holder and the disposable lancet held therein along a predetermined puncture path through a precisely defined longitudinal displacement wherein the tip of the disposable lancet emerges from the needle outlet of the blood withdrawal instrument and past the pressure surface surrounding the outlet into the patients' skin.*

*33. A method according to claim 32 wherein the movement of the lancet holder driven by the lancet drive means and the positioning of the disposable lancet needle tip are so precise, that the puncture depth, the distance the lancet tip emerges past the pressure surface surrounding the outlet, varies by no more than at most 0.15 mm with unchanged setting of the blood withdrawal instrument and successive puncturing movements in which different lancets are inserted in the lancet holder.*

*34. A method according to claim 33, wherein the puncture depth varies by no more than at most 0.1 mm.*

*35. A method according to claim 33, wherein the puncture depth varies by no more than at most 0.05 mm.*

*36. A method according to claim 33, wherein the puncture depth of the tip of the needle of the disposable lancet can be adjusted, without a change in the defined longitudinal displacement, by changing the relative position of the pressure surface and the lancet holder.*

*37. A method according to claim 36, wherein the puncture depth may be adjusted in an adjustment range including values below 2 mm.*

*38. A method according to claim 37, wherein the adjustment range extends below 1.3 mm.*

*39. A method according to claim 32, wherein the pressing of the disposable lancet is obtained by a pair of tongue lugs extending from the lancet holder that penetrate into recesses in the plastic body of the disposable lancet for gripping the plastic body and urging the flat rear end of the needle of the disposable lancet against the stop of the lancet holder.*

*40. A method according to claim 32, wherein rotation of the disposal lancet during operation of the blood withdrawal instrument is avoided by mutually cooperating non-round shapes of an interior space of the blood withdrawal instrument and the plastic body of the disposable lancet.*

*41. The blood lancet device according to claim 9 wherein the lancet drive transmission system maintains contact with the lancet, after the movement to the defined maximum longitudinal displacement, to retract the lancet from the defined maximum displacement reversely along the puncturing direction.*

*42. The blood lancet device according to claim 9 wherein the lancet drive transmission system includes a rotatable input member and a driver output member; wherein the driver output member contacts and moves the lancet; and wherein the driver output member engages the rotatable input member to be longitudinally moved in a straight path to provide the maximum displacement in response to rotation of the rotatable input member.*

*43. The blood lancet device of claim 9 wherein the lancet holder is provided with elastic biasing means to press the lancet positioning means against an output member of the transmission system.*

*44. The blood lancet device of claim 43 wherein the lancet plastic body is provided with a plurality of recesses and wherein the lancet holder is provided with a plurality of tongue lugs that extend into the recesses to provide the biasing means to press the lancet positioning means.*

*45. The blood lancet device of claim 9 wherein the positioning means includes a surface on the lancet, which surface is in contact with and abuts an output member of the transmission system inside the lancet holder to provide the drive from the elastic drive element that moves the lancet.*

*46. The blood lancet device according to claim 9 wherein the housing and the plastic body of the lancet have mutual cooperating and contacting non-round shapes to prevent rotation of the lancet with respect to the housing during the puncturing movement of the lancet tip.*

*47. A method for withdrawing blood for diagnostic purposes by puncturing a patient using the blood lancet device of claim 43, said method comprising:*

*inserting the lancet into the lancet holder with the lancet positioning means engaging the output member of the transmission means and wherein the elastic biasing means presses the lancet positioning means surface against the output member;*

*holding the blood lancet device against the skin of a patient; and*

*actuating the lancet drive means to drive the lancet in the puncture direction through the precisely defined maximum longitudinal displacement, wherein the needle tip will emerge from the blood lancet device and be driven into the skin of the patient.*

*48. A method according to claim 47, wherein the puncture depth can be varied without changing the precisely defined longitudinal displacement by changing the relative position of the fully inserted needle tip with respect to the patient's skin.*

*49. A method according to claim 47, wherein the puncture depth of the needle tip into the patient varies by no more than at most 0.15 mm with unchanged setting of the puncture depth.*

*50. A method according to claim 49, wherein the puncture depth of the needle tip into the patient varies by no more than at most 0.1 mm with unchanged setting of the puncture depth.*

*51. A method according to claim 50, wherein the puncture depth of the needle tip into the patient varies by no more then at most 0.05 mm with unchanged setting of the puncture depth.*

*52. A method according to claim 47, wherein the puncture depth can be adjusted in an adjustment range which includes values of puncture depth below 2 mm.*

*53. A method according to claim 50, wherein the puncture depth can be adjusted in an adjustment range which includes values of the puncture depth below 1.3 mm.*

*54. The blood lancet device of claim 9 wherein the lancet drive means provides a positive drive connection for the lancet to move the lancet along its predetermined path through a first movement in the puncturing direction and a subsequent stopping and retraction of the lancet back into the housing.*

*55. The blood lancet device of claim 17 wherein the lancet drive means provides a positive drive connection for the lancet to move the lancet along its predetermined path through a first movement in the puncturing direction and a subsequent stopping and retraction of the lancet back into the housing.*

*56. The method according to claim 18 wherein the lancet drive means provides a positive drive connection for the lancet to move the lancet along its predetermined path through a first movement in the puncturing direction and a subsequent stopping and retraction of the lancet back into the housing.*

*57. The method according to claim 25 wherein the lancet driver output member connection positively drives the lancet along its predetermined straight path in a first puncturing direction and subsequently stops and then retracts the lancet.*

*58. The method according to claim 32 wherein the lancet drive means also subsequently stops movement of the lancet holder and then retracts the lancet holder to withdraw.*

* * * * *